(12) United States Patent
Azuma et al.

(10) Patent No.: US 11,614,446 B2
(45) Date of Patent: Mar. 28, 2023

(54) IMMUNOCHROMATOGRAPHIC TEST DEVICE

(71) Applicant: SEKISUI MEDICAL CO., LTD., Tokyo (JP)

(72) Inventors: Kanako Azuma, Tokyo (JP); Shinya Okuyama, Tokyo (JP); Kazunori Saito, Tokyo (JP); Keigo Kohno, Tokyo (JP); Motoki Morita, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 289 days.

(21) Appl. No.: 16/766,901

(22) PCT Filed: Dec. 14, 2018

(86) PCT No.: PCT/JP2018/046022
§ 371 (c)(1),
(2) Date: May 26, 2020

(87) PCT Pub. No.: WO2019/117275
PCT Pub. Date: Jun. 20, 2019

(65) Prior Publication Data
US 2020/0355679 A1   Nov. 12, 2020

(30) Foreign Application Priority Data

Dec. 15, 2017 (JP) .............................. JP2017-240993
Dec. 15, 2017 (JP) .............................. JP2017-240994

(51) Int. Cl.
*G01N 33/543* (2006.01)
*B01L 3/00* (2006.01)

(52) U.S. Cl.
CPC ...... *G01N 33/54386* (2013.01); *B01L 3/5023* (2013.01); *B01L 2200/026* (2013.01);
(Continued)

(58) Field of Classification Search
None
See application file for complete search history.

(56) References Cited

U.S. PATENT DOCUMENTS

| | | | |
|---|---|---|---|
| 4,981,786 A | 1/1991 | Dafforn et al. | |
| 2002/0132267 A1* | 9/2002 | Wong ................. | G01N 21/8483 435/7.1 |

(Continued)

FOREIGN PATENT DOCUMENTS

| | | | |
|---|---|---|---|
| CN | 202929035 U | * | 5/2013 |
| EP | 0 306 336 A2 | | 3/1989 |

(Continued)

OTHER PUBLICATIONS

CN202929035 English Translation (Year: 2013).*
(Continued)

*Primary Examiner* — Rebecca M Giere
*Assistant Examiner* — Xiaoyan Zou
(74) *Attorney, Agent, or Firm* — Birch, Stewart, Kolasch & Birch, LLP (57) ABSTRACT

To provide an immunochromatographic test device capable of accurate diagnosis even when an excess sample is introduced. Provided is the immunochromatographic test device consisting of: a test strip; a lower housing including a plurality of support bases that support the test strip; and an upper housing including a dropping hole for dropping a sample into the test strip and a detection window in a direction in which the sample introduced from the dropping hole develops on the test strip, wherein a width of the support base that supports portion of the test strip exposed from the detection window is smaller than a width of the test strip, or wherein among the plurality of support bases, the width of the support base arranged on the lower housing between a position corresponding to the detection window and a posi- (Continued)

tion corresponding to the dropping hole is larger than the width of the test strip.

14 Claims, 7 Drawing Sheets

(52) U.S. Cl.
CPC ..... *B01L 2200/141* (2013.01); *B01L 2200/16* (2013.01); *B01L 2300/025* (2013.01); *B01L 2300/069* (2013.01); *B01L 2300/08* (2013.01); *B01L 2300/0825* (2013.01)

(56) References Cited

U.S. PATENT DOCUMENTS

| | | |
|---|---|---|
| 2013/0230845 A1 | 9/2013 | Egan et al. |
| 2015/0251177 A1 | 9/2015 | Kim et al. |
| 2016/0033501 A1 | 2/2016 | Miyazawa et al. |
| 2017/0212108 A1 | 7/2017 | Li et al. |
| 2017/0315116 A1 | 11/2017 | Shimada et al. |

FOREIGN PATENT DOCUMENTS

| | | |
|---|---|---|
| JP | 64-72066 A | 3/1989 |
| JP | 2002-22743 A | 1/2002 |
| JP | 2008-292197 A | 12/2008 |
| JP | 2009-250763 A | 10/2009 |
| JP | 2012-168051 A | 9/2012 |
| JP | 2012-198159 A | 10/2012 |
| JP | 2013-238543 A | 11/2013 |
| JP | 2014-178153 A | 9/2014 |
| JP | 2015-535078 A | 12/2015 |
| JP | WO 2016/084491 A1 | 6/2016 |
| JP | 2016-161329 A | 9/2016 |
| JP | 2017-173009 A | 9/2017 |

OTHER PUBLICATIONS

Office Action dated Apr. 7, 2021 in Japanese Patent Application No. 2017-240993.
Office Action dated Apr. 7, 2021 in Japanese Patent Application No. 2017-240994.
International Search Report, issued in PCT/JP2018/046022, dated Mar. 19, 2019.
Written Opinion of the International Searching Authority, issued in PCT/JP2018/046022, dated Mar. 19, 2019.
International Preliminary Report on Patentability and English translation of the Written Opinion of the International Searching Authority for International Application No. PCT/JP2018/046022, dated Jun. 25, 2020.
Extended European Search Report for European Application No. 18888926.5, dated Sep. 14, 2021.
Office Action issued in Chinese Patent Application No. 201880080467.8, dated Jan. 11, 2023.

\* cited by examiner

IMMUNOCHROMATOGRAPHIC TEST DEVICE

TECHNICAL FIELD

The present invention belongs to a technical field of immunochromatographic tests using antigen-antibody reactions. More specifically, the present invention relates to a device used for the immunochromatographic tests.

BACKGROUND ART

Immunochromatography is known as a clinical diagnosis method which can make a simple and rapid diagnosis by using specificity based on the immune reactions of antigen-antibody using biological samples such as urine, feces, saliva, blood, serum, and pharyngeal fluid. The immunochromatography is carried out by using the strip, such as nitrocellulose in which a pad impregnated with a first antibody color-labeled with colloidal gold carrier is arranged at one end and a capture site (test line) is arranged at the other end, and dropping a liquid biological sample into the pad, whereby a mixture of the sample, the first antibody, and a complex formed by the antigen-antibody reaction between the antigen in the sample and the first antibody is developed from one end to the other end of the strip by a capillary action. The complex is captured by the antigen-antibody reaction between the antigen and the second antibody at the capture site and accumulates and develops color. The unbound first antibody is captured by a control line arranged downstream of the capture site. Then, the presence or absence of the antigen in the test sample can be determined by observing the degree of the coloration at the capture site of the strip with the naked eye or by an optical detector.

Further, in clinical laboratories, a test strip consisting of an immunochromatography strip is used as a device in which the test strip housed in a housing, typically made of a resin such as plastics in order to test easily. The test device is provided with a dropping hole for dropping an extracted liquid obtained by extracting a sample collected from a patient onto the test strip and a detection window for determining presence of an antigen according to a coloring reaction or the like. Then, a dropping method and a drop amount of a sample extracted solution (hereinafter, referred to as "sample") are defined in detail in the user's manual and the like.

However, when the sample is dropped into the test device in the clinical laboratory, if an excessive amount of the sample is injected into the test device due to an erroneous operation by the operator in charge of testing, accurate test results may not be acquired.

Patent Literature 1 discloses a test container that supports a test strip with a plurality of support bases and has an inclined portion for allowing an excessive sample to flow out toward a rear side of a developing direction. Patent Literature 2 discloses a lateral flow analysis cartridge that is provided with a sub-pad and a sample well for controlling an amount of specimen introduced into a test strip. Patent Literature 3 discloses an immunochromatography test cassette that is provided with a structure in which a part of a peripheral edge of a determination window on a dropping hole side does not contact with a membrane so that the influence of variation in the drop amount can be eliminated.

CITATION LIST

Patent Literature

Patent Literature 1: Japanese Patent Laid-Open No. 2012-168051

Patent Literature 2: National Publication of International Patent Application No. 2015-535078

Patent Literature 3: Japanese Patent Laid-Open No. 2017-173009

SUMMARY OF INVENTION

Technical Problem

When an excessive amount of sample is introduced into the immunochromatographic test device, the test result is adversely affected by various factors. The main object of the present invention is to provide an immunochromatographic test device that can obtain an accurate result even when the amount of sample dropped varies during an immunochromatographic test, particularly when an excessive amount of sample is dropped.

Solution to Problem

As a result of intensive studies, the inventors have found that the above problems can be solved by optimizing the with an immunochromatographic test device comprising an upper housing, a lower housing, and a test strip, in particular, (1) by optimizing a shape of a dropping hole, (2) by optimizing a test strip support base, and (3) by optimizing the structure for guiding an excessive amount of sample, and thus the present invention has been completed. That is, the present invention has the following configuration.

[1] An immunochromatographic test device, comprising: a test strip; a lower housing including a plurality of support bases that support the test strip; and an upper housing including a dropping hole for dropping a sample into the test strip and a detection window in a direction in which the sample introduced from the dropping hole develops on the test strip, wherein a width of the support base that supports portion of the test strip exposed from the detection window is smaller than a width of the test strip, or wherein among the plurality of support bases, a width of the support base arranged between a position corresponding to the detection window in the lower housing and a position corresponding to the dropping hole in the lower housing is larger than the width of the test strip.

[2] An immunochromatographic test device, comprising: a test strip; a lower housing including a plurality of support bases that support the test strip; and an upper housing including a dropping hole for dropping a sample into the test strip and a detection window in a direction in which the sample introduced from the dropping hole develops on the test strip, wherein a width of the support base that supports the portion of the test strip exposed from the detection window is smaller than a width of the test strip.

[3] The immunochromatographic test device according to [2], wherein the width of the support base that supports the portion of the test strip exposed from the detection window is smaller than the width of the test strip by 0.5 mm to 3.0 mm.

[4] The immunochromatographic test device according to [2] or [3], wherein the width of the support base that supports the portion of the test strip exposed from the detection window is smaller than a width of the detection window.

[5] The immunochromatographic test device according to any one of [2] to [4], wherein a height of at least one of the support bases that support the portion of the test strip exposed from the detection window from the lower housing is 0.4 mm or higher.

[6] The immunochromatographic test device according to any one of [2] to [5], wherein a shape of the support base that supports the portion of the test strip exposed from the detection window is a planar shape.

[7] The immunochromatographic test device according to any one of [2] to [6], wherein an area of the support base that supports the portion of the test strip exposed from the detection window is 50% or more of an area of the test strip exposed from the detection window.

[8] An immunochromatographic test device, comprising: a test strip; a lower housing including a plurality of support bases that support the test strip;

and an upper housing including a dropping hole for dropping a sample into the test strip and a detection window in a direction in which the sample introduced from the dropping hole develops on the test strip, wherein among the plurality of support bases, a width of the support base arranged between a position corresponding to the detection window in the lower housing and a position corresponding to the dropping hole in the lower housing is larger than a width of the test strip.

[9] The immunochromatographic test device according to [8], wherein a length in a longitudinal direction of the test strip of the support base arranged on the lower housing between the position corresponding to the detection window and the position corresponding to the dropping hole is longer than ½ of the width of the test strip and smaller than the width of the test strip.

[10] An immunochromatographic test device, comprising: a test strip; a lower housing including a plurality of support bases that support the test strip; and an upper housing including a dropping hole for dropping a sample into the test strip and a detection window in a direction in which the sample introduced from the dropping hole develops on the test strip, wherein the lower housing includes a restricting wall for fixing a position of the test strip, and a thickness of a base portion of the restricting wall on the lower housing side is thicker than a thickness of its tip.

[11] An immunochromatographic test device, comprising: a test strip; a lower housing including a plurality of support bases that support the test strip; and an upper housing including a dropping hole for dropping a sample into the test strip and a detection window in a direction in which the sample introduced from the dropping hole develops on the test strip, wherein the lower housing includes a plurality of restricting walls for fixing a position of the test strip, and a part of the restricting walls arranged on the side of the dropping hole of the test strip for restricting the longitudinal movement of the test strip is left open.

[12] An immunochromatographic test device, comprising: a test strip; a lower housing including a plurality of support bases that support the test strip; and an upper housing including a dropping hole for dropping a sample into the test strip and a detection window in a direction in which the sample introduced from the dropping hole develops on the test strip, wherein the lower housing includes a plurality of restricting walls for fixing a position of the test strip, the restricting wall restricting a longitudinal direction of a dropping hole side is continuous with the restricting wall in a width direction of the test strip on the dropping hole side, and a height of the restricting wall in the width direction is decreased toward a developing direction of the lower housing.

[13] The immunochromatographic test device according to any one of [8] to [12], wherein a height of at least one of the plurality of support bases from the lower housing is 0.6 mm or higher.

[14] An immunochromatographic test device, including: a test strip; a lower housing including a plurality of support bases that support the test strip; and an upper housing including a dropping hole for dropping a sample into the test strip and a detection window in a direction in which the sample introduced from the dropping hole develops on the test strip, wherein the upper housing includes a window frame having inclined portions for dropping a sample around the dropping hole, and the angle of the inclined surface in the developing direction is asymmetric between the upstream side and the downstream side of the development.

[15] The immunochromatographic test device according to [14], wherein the upstream-side inclined portion in the developing direction is less inclined than the downstream-side inclined portion.

[16] The immunochromatographic test device according to any one of [8] to [15], wherein the dropping hole is in a rectangular shape, a width of the dropping hole in a width direction of the test strip is equal to the width of the test strip, and a length of the dropping hole in a longitudinal direction of the test strip is smaller than the width of the test strip.

[17] The immunochromatographic test device according to [16], wherein the window frame is in a semicircular shape.

[18] An immunochromatographic test device, including: a test strip; a lower housing including a plurality of support bases that support the test strip; and an upper housing including a dropping hole for dropping a sample into the test strip and a detection window in a direction in which the sample introduced from the dropping hole develops on the test strip, wherein a inclined portion for observation is provided around the detection window, the inclined portion in a width direction of the device is 30 degrees to 50 degrees, and the inclined portion in a longitudinal direction of the device is 40 degrees to 50 degrees.

[19] An immunochromatographic test device, including: a test strip; a lower housing including a plurality of support bases that support the test strip; and an upper housing including a dropping hole for dropping a sample into the test strip and a detection window in a direction in which the sample introduced from the dropping hole develops on the test strip, wherein a restricting wall lower than a height of the support bases is arranged on a top surface of the lower housing for guiding a leaked sample liquid.

Advantageous Effects of Invention

The immunochromatographic test device according to the present invention (hereinafter, referred to as a "device of the present invention") has its optimum housing structure, so that accurate results can be obtained even if the drop amount of the sample extracted from the patient is not appropriate.

BRIEF DESCRIPTION OF DRAWINGS

FIG. 1A to FIG. 1C are diagrams illustrating a lower housing of a device of the present invention, in which

FIG. 2A to FIG. 2C are diagrams illustrating an upper housing of the device of the present invention, in which

FIG. 3A and FIG. 3B are diagrams showing an example of a test strip used in immunochromatography, in which

DESCRIPTION OF EMBODIMENTS

Hereinafter, the present invention will be described by referring to the accompanying drawings.
<Device of Present Invention>

Figure 1A:
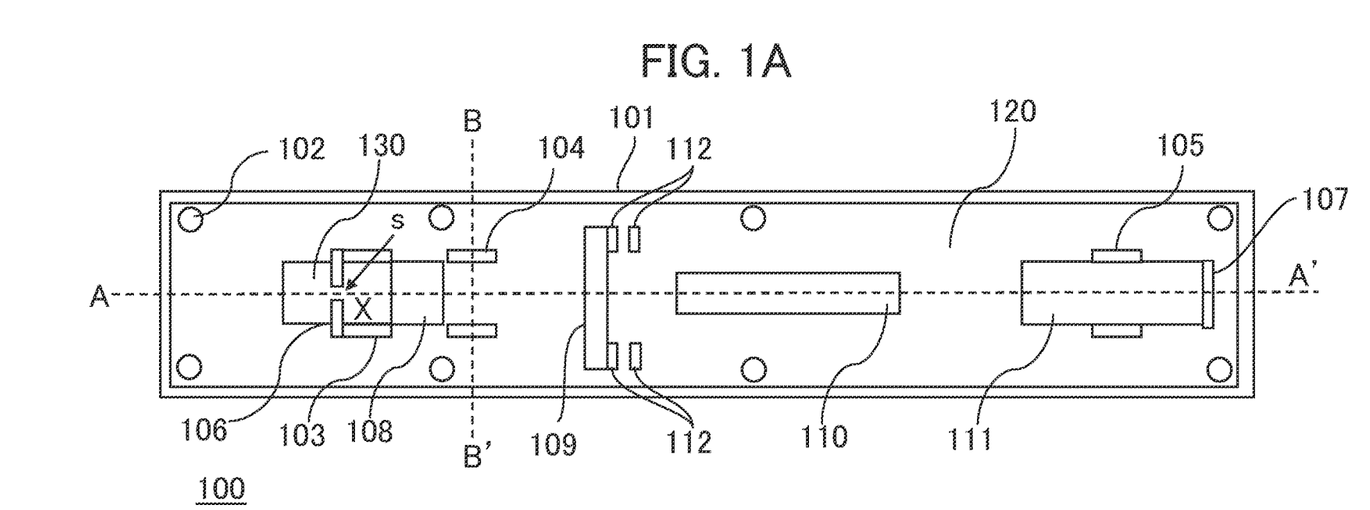
FIG. 1A is a top view.

The device of the present invention comprises an immunochromatographic test strip 150 (Hereinafter, it is sometimes simply referred to as a "test strip".), a lower housing 100 for mounting the test strip in a predetermined position, and an upper housing 200 for covering the lower housing on which the test strip is mounted. FIG. 1A is a top view of the lower housing, FIG. 1B is a sectional view of a dashed line A-A' of the lower housing, FIG. 1C is a side view of the lower housing, FIG. 2A is a top view of the upper housing, FIG. 2B is a rear view of the upper housing, and FIG. 2C is a side sectional view of the dashed line C-C' of the upper housing.

Figure 1B:
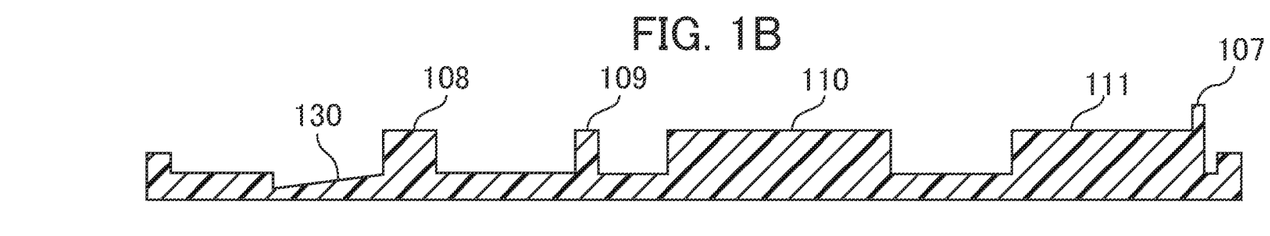
FIG. 1B is a sectional view taken along a dashed line A-A'.
Figure 1C:
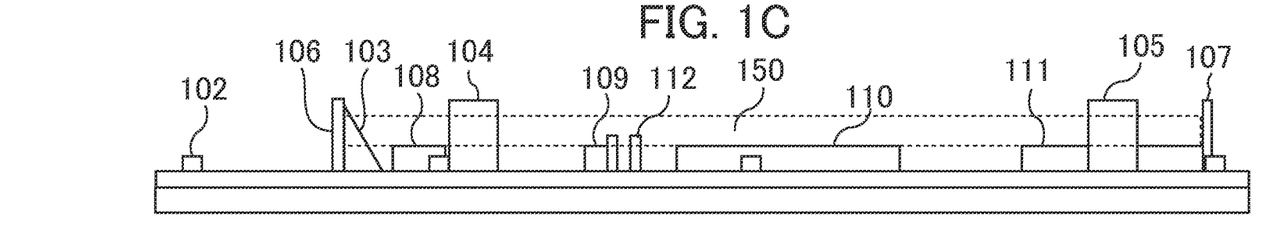
FIG. 1C is a side view.

FIG. 1A to FIG. 1C show a configuration of the lower housing 100. The lower housing 100 comprises: a lower housing main body 101; fixing projections 102 (arranged at eight points in the periphery of the housing in this figure); a pair of first restricting walls 103, a pair of second restricting walls 104, and a pair of third restricting walls 105 for restricting the movement of the test strip in the width direction; a fourth restricting wall 106 and a fifth restricting wall 107 for restricting the longitudinal movement of the test strip; a support base 108, a support base 109, a support base 110, and a support base 111 for placing the test strip above the top surface of the lower housing main body 101; a pair of convex portion 112 provided on both sides of the test strip in the width direction; and a water retention recess 130. In FIG. 1C) (side view), a state in which the test strip 150 is mounted on the housing main body 101 is shown by dashed lines.

Figure 2A:
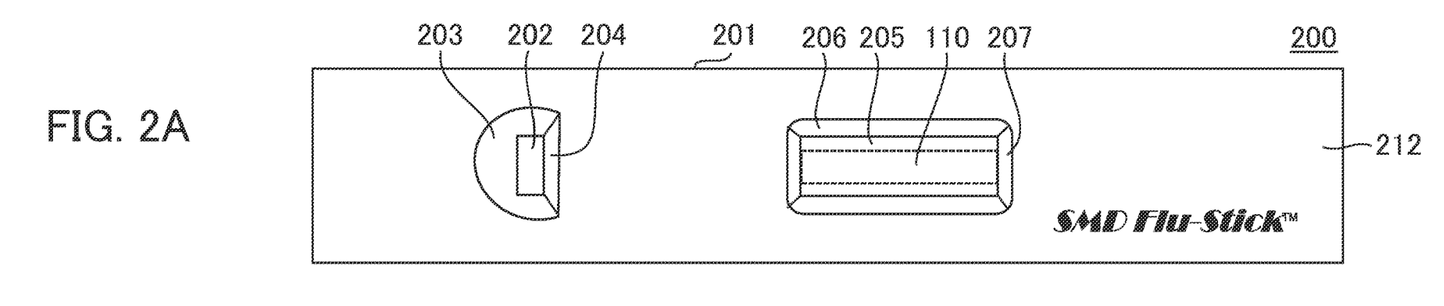
FIG. 2A is a top view.
Figure 2B:
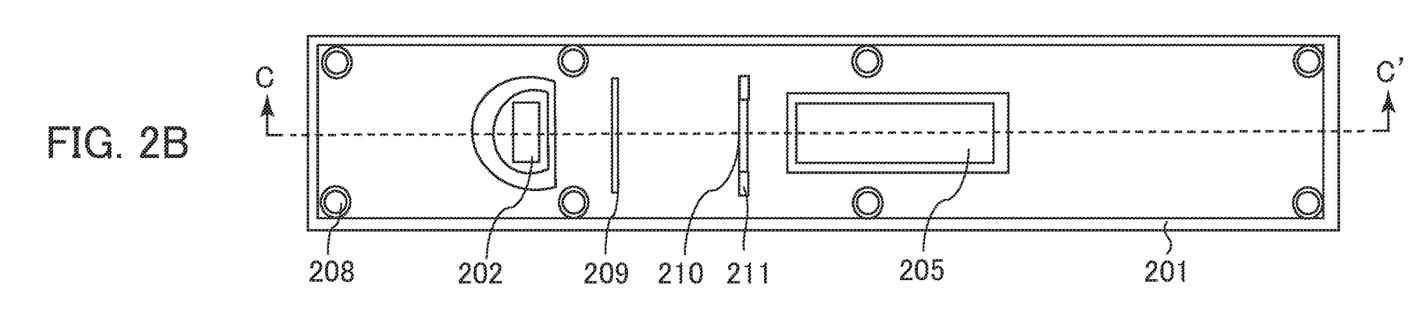
FIG. 2B is a back view.
Figure 2C:
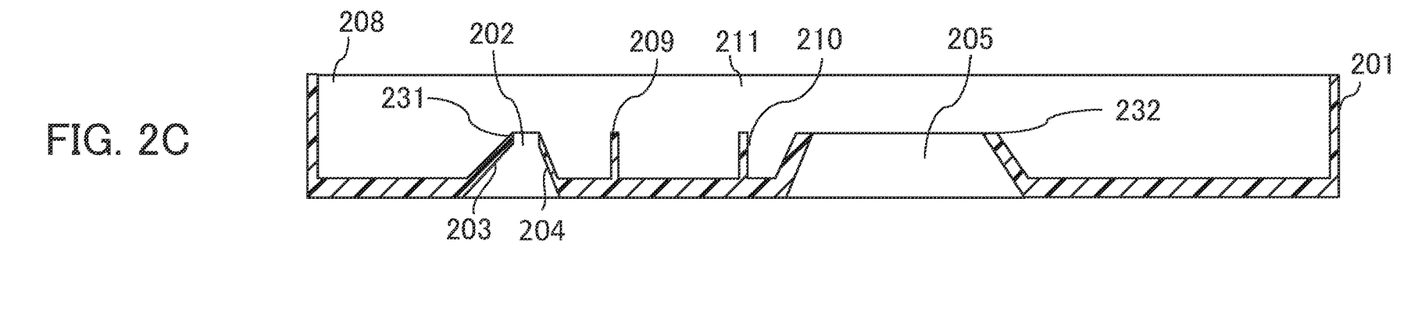
FIG. 2C is an end view taken along a dashed line C-C'.

FIG. 2A to FIG. 2C show a configuration of the upper housing 200. The upper housing 200 comprises: an upper housing main body 201; a dropping hole 202 for dropping a sample; the inclined portion 203; the inclined portion 204; a detection window 205 from which the test strip is exposed to check the presence or absence of a reaction; the inclined portion 206; the inclined portion 207; the holes 208 provided in the periphery of the upper housing (eight points in this figure) for engaging the fixing projections 102 of the lower housing body 101 and locking the upper housing main body 201 and the lower housing main body 101; convex portion 209 and 210 for pressing the test strip 150 toward the lower housing side; a convex portion 211 housed between the pair of convex portion 112 of the lower housing; and a top surface 212 of the upper housing.

<Immunochromatographic Test Strip (Test Strip)>

Figure 3A:
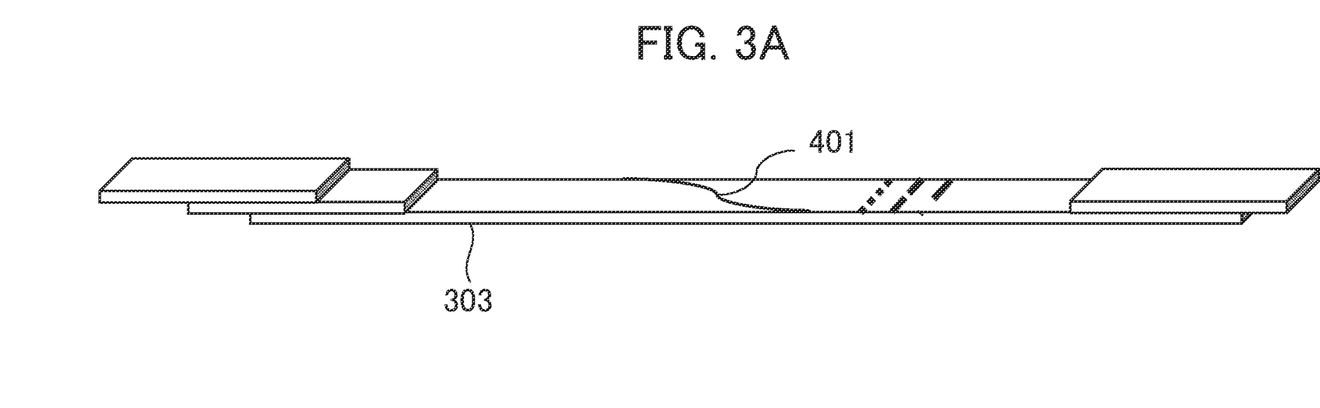
FIG. 3A is a perspective view of the test strip.
Figure 3B:
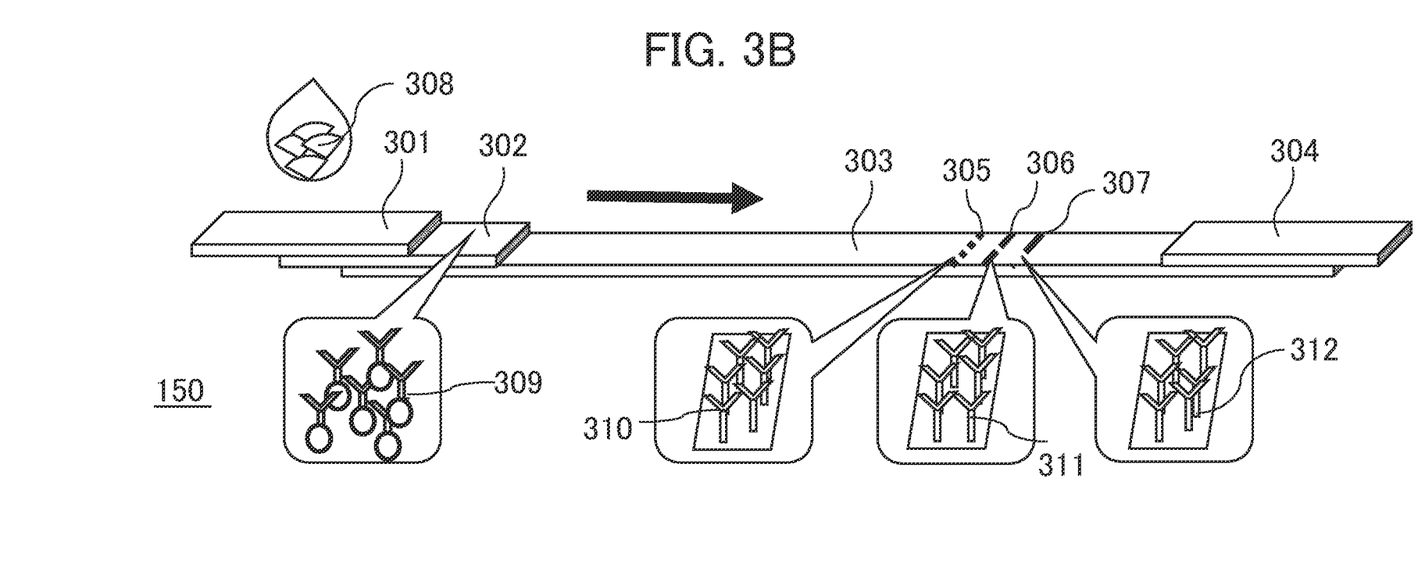
FIG. 3B is a perspective view showing a state of use.

An example of an immunochromatographic test strip for diagnosing influenza is shown in FIG. 3A and FIG. 3B. When a sample solution obtained by diluting a patient sample (in this case, antigen 308 derived from influenza A) is dropped onto a sample pad 301 of the test strip, the sample solution penetrates the conjugate pad 302 impregnated with a colloidal gold labeled antibody 309, and the colloidal gold labeled antibody 309 and the antigen (analyte) 308 bind to form a complex. Subsequently, the complex with a solution reaches the membrane 303 made of nitrocellulose or the like, and is developed on the membrane by a capillary action in the arrow direction (development direction). The solution flow is shown as 401 in FIG. 3A. Antigen 308 then binds to any of capture antibodies 310 and 311 that have been immobilized to test line 1 (TL1) 305 and test line 2 (TL2) 306. Since the capture antibody 310 has a specificity for the influenza A virus, and the capture antibody 311 has a specificity for the influenza B virus, when the antigen 308 is derived from the influenza A virus, it binds to the capture antibody 310, and the TL1 305 is colored. Further, the unreacted labeled antibody reaches the control line (CL) 307 and binds to the immobilized antibody 312 having the specificity for the labeled antibody and CL 307 is colored, so that it is the developed state can be grasped. Further, the sample solution is absorbed by an absorption pad 304.

<Appearance of Housing>

The immunochromatographic device according to the present invention comprises a complex of the lower housing 100 and immunochromatographic test strip 150 mounted on the lower housing 100 and the upper housing 200 arranged to cover the test strip 150 mounted thereon, and has the dropping hole 202 for introducing the sample into the sample pad of the test strip and the detection window 205 for visually or optically detecting the coloration state of the test lines 305, 306 and the control line 307.

The dropping hole 202 is formed for supplying the sample to the test strip 150, and as long as it play role of introducing the sample, the shape and the forming portion are not limited, but it is convenient dropping hole to have a rectangular shape such as an ellipse or a rectangle having a width substantially equal to the width of the test strip in terms of uniformly introducing the sample into the width direction of the test strip. Of these, the rectangular shape is preferable. In the rectangular shape of the dropping hole, the width of the dropping hole in the width direction of the test strip is preferably equal to the width of the test strip, and a length of the dropping hole in the longitudinal direction of the test strip is preferably smaller than the width of the test strip. In FIG. 2A, reference numeral 202 denotes the dropping hole with long sides equal to the width of the test strip and short sides less than the width of the test strip.

Further, it is preferable that a window frame having an inclination is provided around the dropping hole, and the window frame has a rounded semicircular shape so that the dropping operation can be easily performed. In FIG. 2A, the semicircular window frame is formed on the upstream side of the developing direction by the inclined surfaces 203 and 204. By adopting a rectangular shape of the dropping hole and a rounded semicircular shape of the window frame, it becomes easy to drop the sample and uniform development on the test strip becomes possible.

Further, it is preferable that the inclined portion in the longitudinal direction of the window frame (longitudinal direction of the device) around the dropping hole 202 has a gentle inclined portion 203 for handling of sample introduction and the steep inclined portion 204 for securely introducing sample from the inclined portion to the dropping hole. It is desirable that the gentle inclined portion slopes between 15 degrees and 45 degrees with respect to the top surface 212 of the upper housing, and that the steep inclined portion slopes between 45 degrees and 90 degrees with respect to the top surface 212 of the upper housing. The angle of inclination is preferably in the range described above, but may have a plurality of slopes intermittently or continuously from a more gentle angle to a final angle thereof. As described above, by making the inclination of the introduction portion into the dropping hole asymmetric with respect to the longitudinal direction of the device, both the handling of the dropping operation and proper introduction of the sample can be achieved. That is, when the sample is introduced from the gentle inclined portion by a dropper or pipette, since dropping onto the test piece can be confirmed, and because of the steep inclined portion, the sample falls and is easily introduced into the test strip.

Further, it is especially convenient that the distance between the test strip 150 and the bottom portion 231 of the dropping hole 202 is set to 0 to 0.8 mm so that the sample can be easily introduced into the sample pad 301.

The detection window 205 is formed so as to be able to visually or optically detect the coloration state of the test line 305, 306, and the control line 307 of the test strip 150, and the number, shape, formation region, and the like of the opening are not limited as long as it serves as the detection window. For example, in present embodiment, an opening having a shape along the longitudinal direction of the test strip in which each line can be confirmed at the same time is shown, but the opening may be an opening in which each line, a plurality of lines are simultaneously exposed or only a part of the lines are exposed.

Further, the inclined portion 206 and 207 around the detection window 205 is advantageously sloped gently, preferably degrees to 60 degrees relative to the top surface of the housing.

When a length of the opening of the detection window is about the same as the width of the test strip 150, if the angle of the inclined portion (for example, the inclined portion 207) is set to 40 degrees to 50 degrees, the test strip can be visually or optically detected from outside without the shadow of the upper housing falling on the membrane. Similarly, when the length of the opening is twice or more of the width of the test strip, the angle of the inclined portion (for example, the inclined portion 206) is preferably 30 degrees to 60 degrees. As these angles, there may be a plurality of slopes intermittently or continuously from a more gentle angle to a final angle thereof. Especially, when optical detection is performed, since light must be irradiated from an oblique direction, the configuration in which shadows are difficult to form is more important.

Further, in order to prevent the shadow of the upper housing from being cast on the test strip 150, the distance between the test strip 150 and the bottom portion 232 of the detection window 205 is preferably 0 to 2.0 mm, and more preferably 0 to 0.5 mm. However, in the case where the test strip is sandwiched between the bottom portion 232 and the support base 110 of the lower housing, it is preferable to prevent the bottom portion from contacting the test strip so as not to press the test strip, because this will not affect the development of the sample on the test strip. Further, the surface of the detection window 205 can be covered with a transparent plastic or the like to form a window not released into the air. This can reduce the external influence on each line.

The material of the housing of the device of the present invention is preferably an opaque synthetic resin such as plastic, and may be acrylic, polyethylene, polypropylene, polystyrene such as high impact polystyrene, PET, or the like, or a combination thereof, or a synthetic resin in which an appropriate amount of filler is added.

Further, the housings of the embodiment can be formed by injection molding or by cutting from a bulk member. Further, when the constituent members are made of different materials, they can be formed by integral molding. Although one test strip is mounted in this embodiment, a plurality of test strips may be arranged in the width direction of the test strips.

<Internal Configuration of Housing>
<Lower Housing>

The lower housing 100 has a configuration for holding the test strip 150.

1. Restricting Wall

The restricting walls 103 to 107 have a function of restricting in-plane movement of the test strip 150 arranged in the lower housing 100. The restricting wall may be arranged at least at one in front of and behind the longitudinal direction of the test strip (restricting walls 106, 107). Further, in the width direction of the test strip, it is sufficient that the restricting walls are arranged at least in a pair on the side surface of the test strip, and FIG. 1A to FIG. 1C show an example where three pairs thereof are arranged in the longitudinal direction (restricting walls 103, 104, and 105).

Figure 4A:
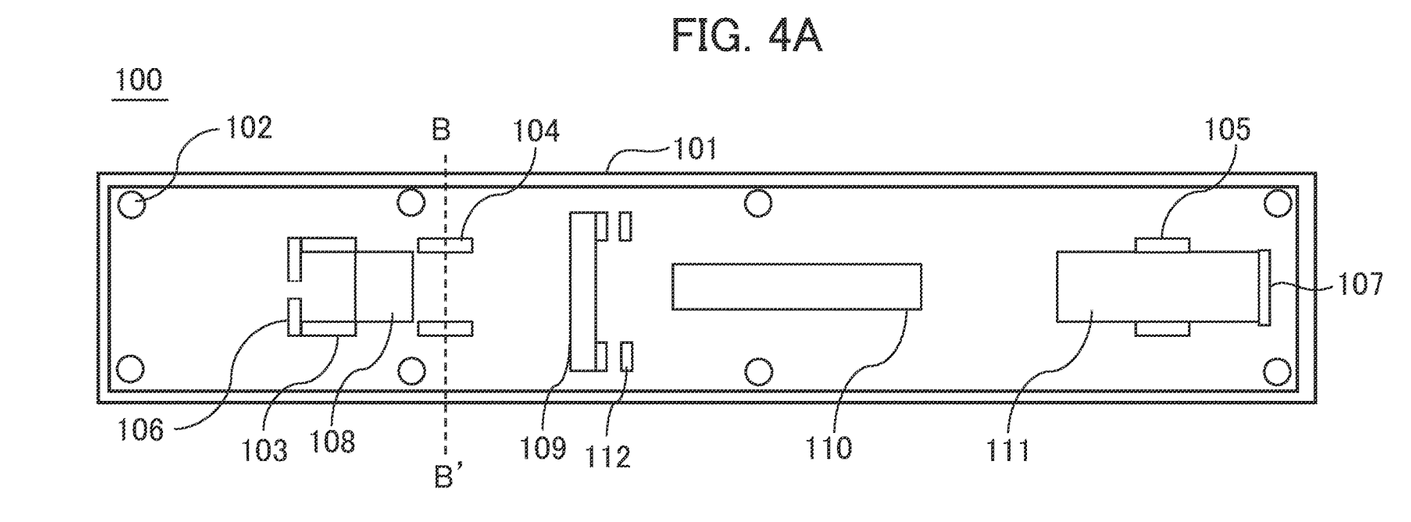
FIG. 4A is a top view of the lower housing of the device according to the present invention.
Figure 4B:
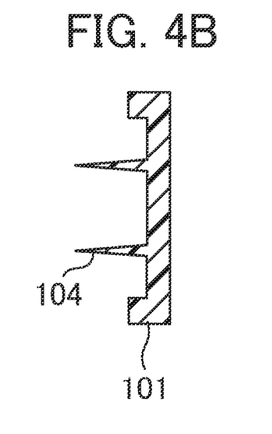
FIGS. 4B, FIG. 4C, FIG. 4D, FIG. 4E, and FIG. 4F are sectional views of variations of a restricting wall 104 taken along a dashed line B-B'.
Figure 4C:
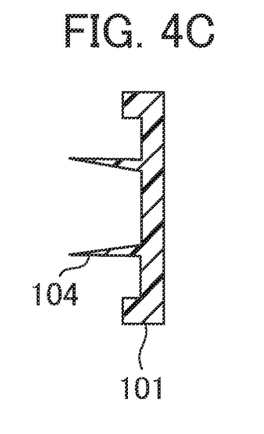
Figure 4D:
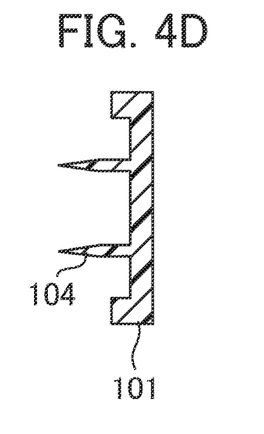
Figure 4E:
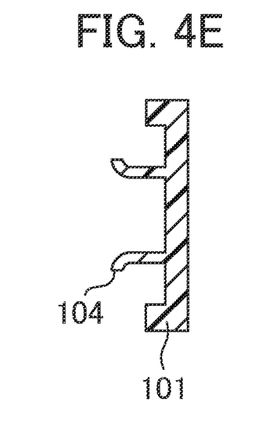

Variations of the standing structure of the restricting wall according to the embodiment are shown in FIG. 4B to FIG. 4F as vertical sectional views at the position indicated by dashed line B-B' in FIG. 4A. In these figures, the top portion of each of the restricting walls 104 is arranged to be away from the test strip to be inserted as compared with the base portion, so that the test strip can be easily inserted between the restricting walls. Regarding the sectional shape pf the restricting walls 104, FIG. 4B is an example of an isosceles triangle, FIG. 4C is an example of a vertical triangle with vertical outside, FIG. 4D is an example in which the tip portion of FIG. 4B is made thinner, and FIG. 4E is an example in which the tip portion is bent outward with the same thickness from the base to the tip.

Figure 4F:
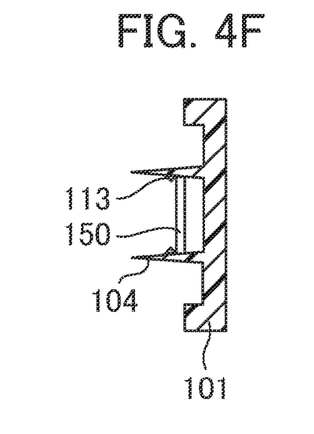

FIG. 4F shows an example in which the projection 113 is provided just above the height at which the test strip 150 is positioned to prevent the test strip from being deviating from the normal position. In FIG. 4F, reference numeral 113 denotes a projection, but it may be a linear projection protruding to the same height.

Although the restricting walls 104 are shown as an example, other restricting walls can have the same structure. The restricting walls are preferably injection molded from the same material as that of the lower housing, but plate-like restricting walls made of a metal sheet such as aluminum may be integrally molded with the resin of the lower housing. In such case, the test strip can be inserted and held by deforming the shape of the restricting walls and then deforming the restricting walls to the original shape.

Further, referring to FIG. 1A, the restricting walls 103 and the restricting walls 106 have a space for housing an end portion of the test strip on the sample dropping side, and the excess sample can be retained in an area "X" partitioned thereby. Note here that when an excess sample exceeding the maximum retaining amount of the area "X" is injected, the excess sample is discharged from a gap "s" provided between the restricting walls 106. The gap "s" may be provided in a part of the restricting walls 106, and preferably in the center. Further, in the embodiment, the height of the restricting walls 103 is lowered toward the developing direction as shown in FIG. 1C so that the extra sample retained in the area "X" does not leak out further in the developing direction through the support base 108, and most of the reatained sample is adsorbed and retained on the rear restricting walls 106 by the surface tension. In addition, the water-absorbent pad may be arranged on the top surface of the area "X" or outside the gap "s" to reduce the influence of leakage. Further, the recess 130 communicating with the gap "s" is provided in the area "X", so that the excess sample is retained in the recess 130.

2. Support Base

The support base 108 to 111 serve to support the test strip away from the top surface of the lower housing main body 101. Thereby, it is possible to prevent the sample leaked from the sample pad and flown out of the original developing route of the test strip from reaching the test strip again through the top surface of the lower housing main body. As a result, a risk of misdiagnosis can be reduced. It is preferable that the support bases have elements for supporting at least three positions, that are a lower portion of the dropping hole, a lower portion of the test lines and the control line, and a lower portion of the end of the development direction of the test strip(adsorption pad). When the height of the support bases mounting surface from the top surface of the lower housing is 0.4 mm or more, preferably 0.6 mm or more, the influence of the excess sample can be avoided. Because of the restriction of the height of the housing, the height of the support bases is preferably to be 2 mm or less.

Figure 5:
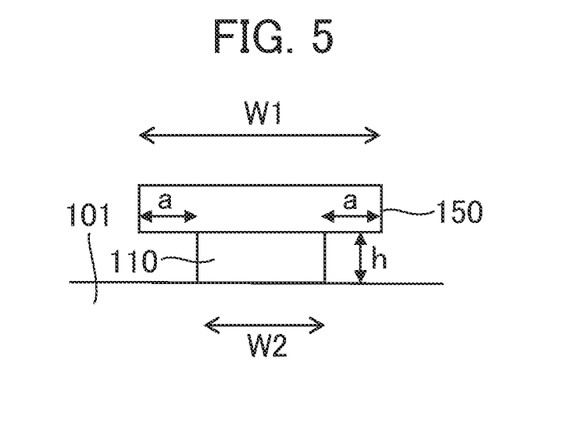
FIG. 5 is a diagram showing the relationship between the width of one support base and the test strip according to the present invention.

Referring to FIG. 5, the width (W2) in the width direction (width direction of the test strip) of the support base 110 that supports the portion of the test strip exposed from the detection window is preferably smaller than the width (W1) of the test strip, and more preferably smaller than the width of the detection window. With this configuration, the area of the test strip sandwiched between the bottom portion of the detection window of the upper housing in the width direction and the support base 110 is reduced and preferably eliminated, and it is possible to prevent a difference in the development speed of the sample in the width direction of the test strip due to an unintended pressing force being applied to the test strip. The length "a" at which the test strip protrudes from the support base 110 is preferably from 0.25 mm to 1.5 mm, more preferably from 0.5 mm to 1.2 mm, and still more preferably from 0.5 mm to 1.0 mm per side. Therefore, the width of the support base for supporting the portion of the test strip exposed from the detection window is preferably smaller than the test strip by 0.5 mm to 3.0 mm, more preferably by 1.0 mm to 2.4 mm, and still more preferably by 1.0 mm to 2.0 mm.

Further, the height "h" of the support base 110 is preferably 0.4 mm or more, more preferably 0.6 mm or more, and still more preferably 0.8 mm or more.

The support base 110 for supporting the portion of the test strip exposed from the detection window may be formed of a planer body such as a rectangular parallelepiped, several linear bodies or a group of point bodies. Among them, the planar body is preferable. The width of the support base in the cases of a linear body or a point body may be such that the distance between outermost portions of the linear body or the point body is smaller than the width of the test strip. The top surface of the planar body, that is, the surface in contact with the test strip, may be a smooth plane or an embossed surface that support the test strip by point contact.

It is desirable that the support base that supports the portion of the test strip exposed from the detection window is brought into contact with the test strip in an area and with a space with which the test strip at an area and a space such that the test strip does not bend due to weight when the test strip absorbs the sample. The area of the support base is desirable to be 50% or more of the area of the test strip exposed from the detection window, and more preferable to be 80% or more. Further, when the support base is the point bodies or the linear bodies other than the planar body, it is desirable for the contact area between the area of the test strip and the support base to be 50% or more with respect to the area of the test strip exposed from the detection window.

Referring to FIG. 1A and FIG. 1B, in the embodiment, the support base 109 is arranged in addition to the support bases 108, 110, and 111. The support base 109 is arranged between the position corresponding to the detection window of the upper housing and the position corresponding to the dropping hole, and the width of this support base is desirably larger than the width of the test strip. The width of this support base is desirably 0.5 mm to 5 mm larger than the width of the test strip, and may be, for example, 1 mm to 4 mm or 2 mm to 4 mm. The support base 109 has a function (rectification) of preventing the sample from entering in the developing direction of the device when the sample excessively introduced in the sample pad leaks, and reducing the difference in the developing speed of the sample in the width direction on the test strip on the support base 109. For proper rectification, the length of the support base 109 in the longitudinal direction (longitudinal direction of the test strip) is preferably ⅓ or more, and more preferably ½ or more, of the width of the test strip 150.

Further, it is convenient that the support base 109 positioned closer to the support base 110 than the intermediate point of the support base 108 and the support base 110.

Preferably, the support base is injection molded of the same material as that of the lower housing, but may be integrally molded of a metal, glass, ceramic, or the like made of materials that do not react with the sample.

<Upper Housing>

Referring to FIG. 2A to FIG. 2C, the convex portion 209 and 210 are provided on the upper housing for pressing the test strip 150 toward the lower housing side.

3. Convex Portion

The convex portion 209 and the convex portion 210 prevent the test strip 150 from being floated from the lower housing 100. That is, in the test strip 150 shown in FIG. 3B, the sample pad 301 is prevented from being floated from the conjugate pad 302, and conjugate pad 302 is prevented from being floated from the membrane 303. Further, since the convex portion 209 and the convex portion 210 have the same length as the width of the test strip, it is possible to prevent the leaked sample from developing on the membrane 303 through the upper part of the test piece 150, or reaching the front side of the control line of the test strip through the inner surface of the upper housing 200 and adversely affecting the test result.

4. Dropping Hole

The bottom portion 231 of the dropping hole 202 is designed to be close to the surface of the test strip 150 mounted on the device at the distance of 0 mm to 1 mm. Since the width of the dropping hole in the width direction of the test strip 150 is designed to be between the size smaller than the width of the test strip by about 3 mm and the size subsequentially equal to the width of the test strip, the sample is uniformly introduced into the test strip in the width direction of the test strip. A width of a dropping window in the longitudinal direction of the test strip is designed to be 2 mm to 4 mm for enabling uniform introduction toward the longitudinal direction.

5. Detection Window

The bottom part 232 of the detection window 205 is designed to be close to the surface of the test strip 150 mounted on the device at a distance of 0 mm to 2 mm. Thus, the floating of the test strip 150 can be prevented by the bottom portion 232 of the detection window 205. Since the width of the opening in the width direction of the test strip 150 is designed to be approximately 1.5 mm to 0.5 mm smaller than the width of the test strip, dust or the like does not enter the inside of the housing from the gap. Further, since the detection window 205 and the support table 110 are not excessively overlapped with each other, a non-uniform load is not applied to the test piece, so that the judgment result is not affected.

(Evaluation Experiment 1)

A following experiment was performed in order to investigate the relation between the height of the support base 110 that supports the portion of the test strip exposed from the detection window and creeping of a sample extracted solution toward the periphery of the test strip.

1. Experiment Method (1) Test Device

The test device used consisted of the upper housing 200, the lower housing 100 according to the present invention and the support bases 108 to 111 which fixed the test strip 150 inserted to the upper housing 200 and the lower housing 100. The width of the test strip was set to be almost the same as the width of the support bases (W1=W2 in FIG. 5). The height of the support base 110 (h in FIG. 5, the height of the position of the mounting surface of the support base from the top surface of the lower housing 101) was set to 0 mm to 0.9 mm in 0.3 mm increments. A line was drawn with a marker pen behind the position of the test line where the antibody was immobilized in the test strip in order to check a failure due to leakage of the sample extracted solution.

(2) Evaluation Method

Originally, the amount of the sample to be dropped into the device was three drops (80 to 120 μl) of the sample extracted solution, but five drops of physiological saline were dropped from the dropping hole, and same operations as in the clinical examination was performed, and the test device left for 10 minutes was opened to observe the test strip, and if the line drawn with the marker pen on the back of the test strip was blurred, the device was judged as incompatible, and if it was not blurred, the device was judged as compatible. The experiment was repeated three times for each test device with each height of the support base.

TABLE 1

| Height "h" of support base | Failure caused by leakage of sample (3 each in total) |
|---|---|
| 0 mm | 3 |
| 0.3 mm | 3 |
| 0.6 mm | 0 |
| 0.9 mm | 0 |

2. Experimental Result

The result is shown in Table 1. From the result, it is found that the height of the support base that supports the portion of the test strip exposed from the detection window (the height of the test strip mounting surface of the support base from the top surface of the lower housing) is preferable to be higher than 0.3 mm, more preferable to be higher than 0.4 mm or more, and still more preferable to be higher than 0.6 mm or more. It is because it is possible to avoid the influence of the excess sample flowing through the top surface of the lower housing. Note that it is convenient for the upper limit of the height of the support base to be 2 mm or less due to the restriction of the height of the housing. While the physiological saline was used in this experiment, similar results were acquired by using other extraction solutions.

(Evaluation Experiment 2)

A following experiment was performed to investigate the relationship between the height of the support base 110 supporting the portion of the test strip exposed from the detection window and leakage of a sample extracted solution around the test strip. The difference from the Evaluation Experiment 1 was that the width of the support base 110 was set smaller than that of the test strip.

1. Experiment Method (1) Test Device

The test device used consisted of the upper housing, the lower housing, the test strip inserted thereto, and the support base 110 according to the present invention, in which the width of the support base 110 was set to be smaller by 1 mm each from both ends of the test strip. That is, in FIG. 5, W1=W2+2 (mm) and a=1 (mm). The height of the support base 110 ("h" in FIG. 5, the height of the position of the mounting surface of the support base from the top surface of the lower housing 101) was set to 0 mm to 1.2 mm in 0.2 mm increments.

(2) Evaluation Method

Originally, the amount of the sample to be dropped into the device was three drops (80 to 120 μl) of the sample extracted solution, but five drops of physiological saline were dropped from the dropping hole, and same operations as in the clinical examination were performed, and the test device left for 10 minutes was observed visually from the detection window, and the device in which the test strip absorbed water from both ends was judged as incompatible, and the device in which the specimen did not absorbed water from both ends was judged as compatible. The experiment was repeated ten times for each test device with each height of the support base.

TABLE 2

| Height "h" of support base | Failure caused by leakage of solution (10 each in total) |
|---|---|
| 0 mm | 10 |
| 0.2 mm | 8 |
| 0.4 mm | 2 |
| 0.6 mm | 1 |
| 0.8 mm | 0 |
| 1.0 mm | 0 |
| 1.2 mm | 0 |

2. Experimental Result

The result is shown in Table 2. From the result, it was found that the height of the support base (the height of the support base from the top surface of the lower housing) supporting the portion of the test strip exposed from the detection window 205 may be 0.4 mm or more, preferably 0.6 mm or more, and more preferably 0.8 mm or more. The influence of the excess sample could be avoided with such height. In addition, it is convenient that the upper limit of the height of the support base is 2 mm or less due to the restriction of the height of the housing. While the physiological saline was used in this experiment, similar results were obtained using other extraction solutions.

(Evaluation Experiment 3)

A following experiment was performed to investigate the relation between the height of the support base 110 that supports the portion of the test strip exposed from the detection window and the width of the test strip.

1. Experiment Method
(1) Test Device

The test device used consisted of the upper housing and the lower housing according to the present invention and the test strip used for a ordinary test. The height (h in FIG. 5) of the support base 110 was set to 0.6 mm, and the protruding length of the test strip from the support base (a in FIG. 5, distance from the widthwise end of the support base 110 to the widthwise end of the test strip) was set to 0 mm to 1.75 mm in increments of 0.25 mm.

(2) Evaluation Method

Figure 6A:
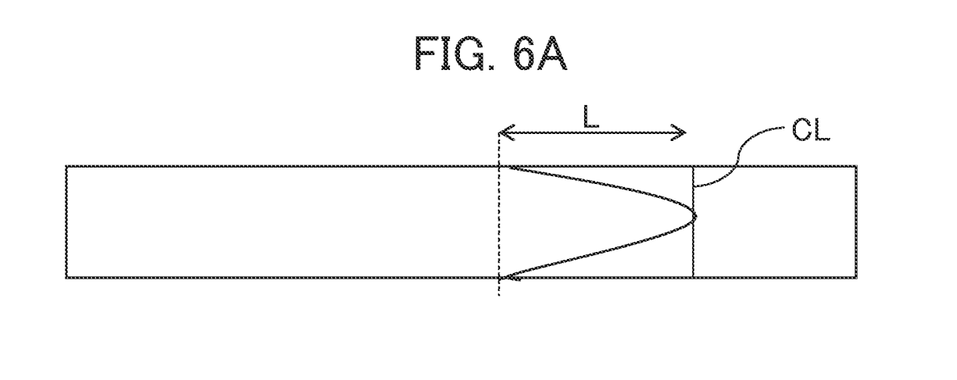
FIG. 6A and FIG. 6B are diagrams showing the difference in development speed on the test strip.
Figure 6B:
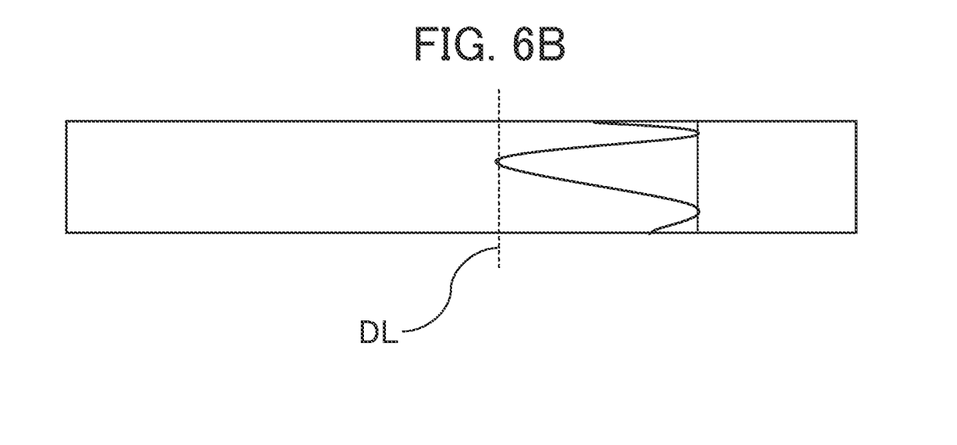

Originally, the amount of the sample to be dropped into the device was three drops (80 to 120 μl) of the sample extracted solution, but five drops of physiological saline were dropped from the dropping hole, and same operations as in the test were performed, and the test device left for 10 minutes was observed visually from the detection window, and the device was judged as incompatible if the distance (L in FIG. 6) between the control line (CL) when the physiological saline reached at the position of the control line and the site (DL) where the arrival of the physiological saline was delayed was 3 mm or more, and the device was judged as compatible if it was less than 3 mm. The experiment was repeated ten times for each test device, and the number of incompatible cases are shown below.

TABLE 3

| Protruding length "a" from support base | Development failure caused by interference between bottom portion of detection window and end portion of test strip | Development failure caused by side leakage or floating |
| --- | --- | --- |
| 0 mm | 8 | 0 |
| 0.25 mm | 2 | 0 |
| 0.5 mm | 0 | 0 |
| 0.75 mm | 0 | 0 |
| 1.0 mm | 0 | 0 |
| 1.2 mm | 0 | 1 |
| 1.5 mm | 0 | 4 |
| 1.75 mm | 0 | 7 |

2. Experimental Result

The result is shown in Table Among the "incompatible" cases, the case in which the development speed in both ends of the test strip in the width direction was slow due to, for example, crashing the both ends of the test strip by the housings was evaluated as "Development failure caused by interference", and the case in which the colloidal gold labeled antibody was not retained at both ends due to, for example, inflow of the sample to the bottom of the housing caused by the contact of one side of the test strip with the bottom of the housing, as "Development failure caused by side leakage or floating" of the test strip.

From the result, it is determined that the optimum value of the protruding length "a" is 0.25 mm to 1.5 mm, preferably 0.5 mm to 1.2 mm, and more preferably 0.5 mm to 1.0 mm. Therefore, the width of the support base for supporting the portion of the test strip exposed from the detection window is preferably 0.5 mm to 3.0 mm smaller than the test strip, more preferably 1.0 mm to 2.4 mm, and still more preferably 1.0 mm to 2.0 mm. A similar tendency was observed even when the height of the support base being 0.4 mm to 1.2 mm.

Modification Example 1

Figure 7A:
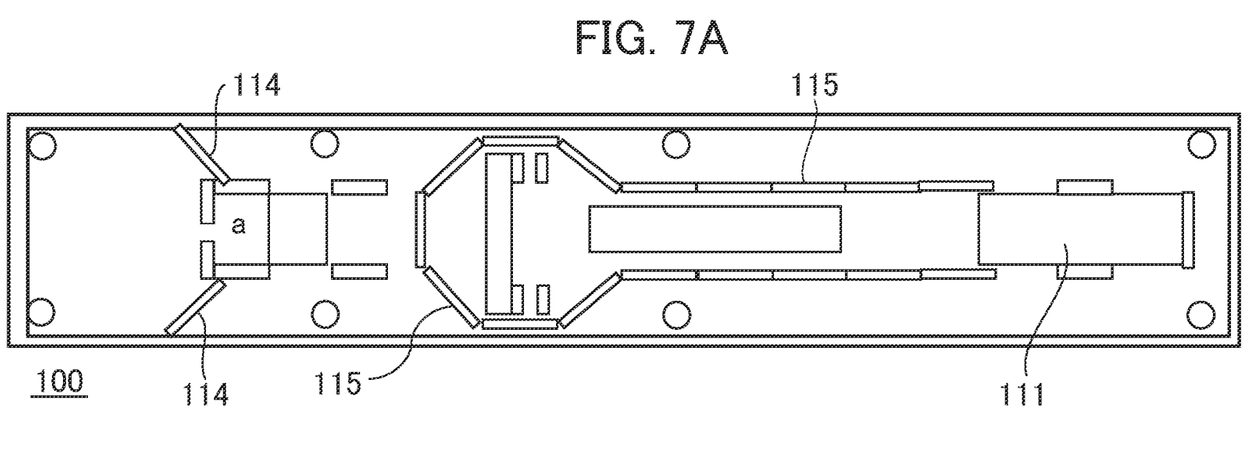
FIG. 7A is a top view of the lower housing.
Figure 7B:
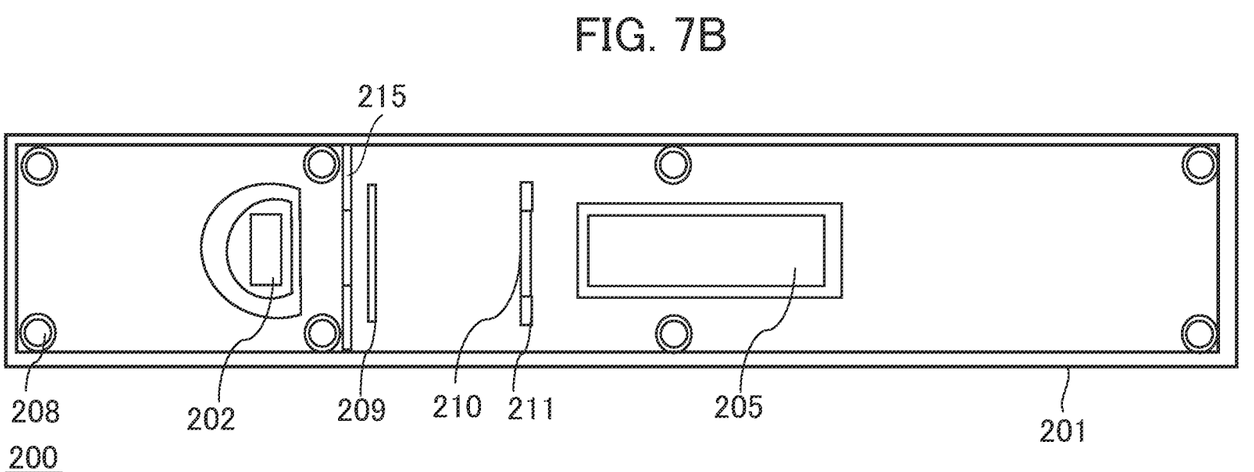
FIG. 7B is a back view of the upper housing showing a modified example regarding the restricting wall of the device of the present invention.

FIG. 7A and FIG. 7B show a configuration of a modification example of the device according to the present invention in which additional convex portions are arranged for controlling the flow of the excess sample.

FIG. 7A shows a case of providing additional convex portions 114 and 115 to the lower housing 100, and FIG. 7B shows a case of providing an additional convex portion 215 to the upper housing 200. All of the convex portion 114, 115, 215 are liquid guiding structures for avoiding the sample leaked from the sample pad to contact the test strip. The height of such auxiliary restricting structures is lower than the height of the support bases and the convex portion 209, 210, so that those structures do not directly contact the test strip. The convex portion 114 of the lower housing 100 particularly prevent the sample leaked from the area "a" where the sample may accumulate from flowing in the development direction of the sample, and the convex portion 115 prevents the dropped sample from leaking and approaching the vicinity of the detection area (Area including the test lines and the control line). The convex portion 215 prevents the sample introduced from the dropping hole leaking along the inner surface of the upper housing from further flowing in the development direction.

Modification Example 2

Figure 8:
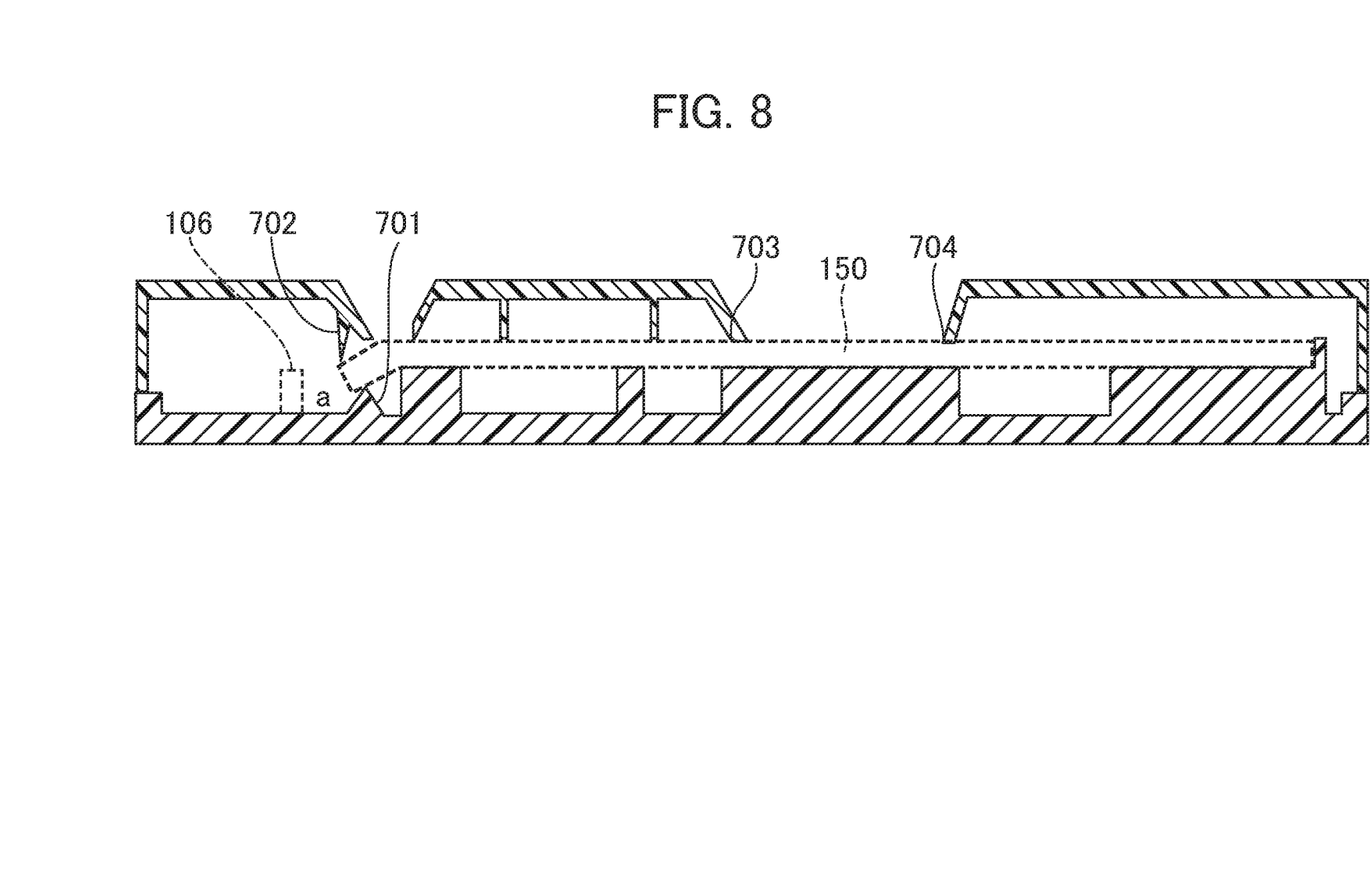
FIG. 8 is a sectional view of the device of the present invention in a state in which the test strip is mounted, and is a diagram showing a modified example of a restricting structure.

FIG. 8 shows a configuration of a modification example of the device according to the present invention in which additional convex portion 701 and 702 are arranged for restricting the test strip 150 in the height direction of the device.

The additional convex portion 701 has a function of guiding the excess sample to the area "a" by making contact with the lower surface of the test strip 150. The additional convex portion 702 is a convex portion protruding from the inner surface of the upper housing toward the test strip 150, and urges the end of the test strip 150 on the opposite side of the development direction toward the lower housing. Thereby, the excess sample is guided to the area "a". Reference numeral 703 denotes a bottom portion located on the sample pad side in the longitudinal direction of the opening of the detection window, which slightly contacts the test strip to prevent floating of the test strip, thereby generating rectification of the sample in the width direction. Reference numeral 704 denotes a bottom portion located on the absorption pad side in the longitudinal direction of the opening of the detection window, which slightly contacts the test strip to prevent the back flow of the sample. Even in this case, it is convenient that the bottom portion of the opening of the detection window in width direction is not in contact with the test strip.

Although the embodiment of the present invention has been described above as an example, it is not intended to limit the scope of the present invention. The above embodiments can be implemented in various other forms, and various kinds of omissions, substitutions, and changes can be made without departing from the gist of the present invention. Further, each configuration, shape, size, length, width, thickness, height, number, and the like can be appropriately changed. Furthermore, each of the embodiments may be combined into a new embodiment.

INDUSTRIAL APPLICABILITY

According to the present invention, it is possible to perform stable and accurate diagnosis even when the drop amount of the sample is not appropriate in the test using the immunochromatographic test device.

REFERENCE SIGNS LIST

100 Lower housing
101 Lower housing main body
102 Fixing projection
103 to 107 First to fifth restricting walls
108 to 111 Support base
112 Convex portion
114 to 115 Additional convex portion
130 Water retention recess
150 Immunochromatographic test strip
200 Upper housing
201 Upper housing main body
202 Dropping hole for dropping sample
203 to 204 Inclined portion
205 Detection window
206 to 207 Inclined portion
208 Hole
209 Convex portion
210 Convex portion
215 Additional convex portion
231 Bottom portion of dropping hole
232 Bottom portion of detection window
301 Sample pad
302 Conjugate pad
303 Membrane
304 Absorption pad
305 Test line 1
306 Test line 2
307 Control line
308 Antigen derived from influenza A
309 Colloidal gold labeled antibody
310, 311 Capture antibody
312 Immobilized antibody
701 to 702 Additional convex portion
703 to 704 Bottom portion of detection window

The invention claimed is:

1. An immunochromatographic test device, comprising:
   a test strip;
   a lower housing comprising a plurality of support bases that support the test strip; and
   an upper housing including a dropping hole for dropping a sample into the test strip and a detection window in a direction in which the sample introduced from the dropping hole develops on the test strip, wherein
   a width of the support base that supports the portion of the test strip exposed from the detection window is smaller than a width of the test strip, and/or
   wherein among the plurality of support bases, the width of the support base arranged between a position corresponding to the detection window in the lower housing and a position corresponding to the dropping hole in the lower housing is larger than the width of the test strip,
   and further wherein the width of the support base that supports the portion of the test strip exposed from the detection window is smaller than the width of the test strip by 0.5 mm to 3.0 mm, and the height of at least one of the plurality of support bases from the lower housing is 0.6 mm or higher.

2. The immunochromatographic test device according to claim 1, wherein the width of the support base that supports the portion of the test strip exposed from the detection window is smaller than a width of the detection window.

3. The immunochromatographic test device according to claim 1, wherein a height of at least one of the support bases that support the portion of the test strip exposed from the detection window from the lower housing is 0.4 mm or higher.

4. The immunochromatographic test device according to claim 1, wherein a shape of the support base that supports the portion of the test strip exposed from the detection window is a planar shape.

5. The immunochromatographic test device according to claim 1, wherein an area of the support base that supports the portion of the test strip exposed from the detection window is 50% or more of an area of the test strip exposed from the detection window.

6. The immunochromatographic test device according to claim 1, wherein a length in a longitudinal direction of the test strip of the support base arranged between the position corresponding to the detection window in the lower housing and the position corresponding to the dropping hole in the lower housing is longer than ½ of the width of the test strip and shorter than the width of the test strip.

7. An immunochromatographic test device according to claim 6, wherein the lower housing includes a plurality of restricting walls for fixing a position of the test strip, and wherein a gap between adjacent restricting walls arranged on the side of the dropping hole of the test strip for restricting the longitudinal movement of the test strip permits leakage of excess sample from said test strip.

8. The immunochromatographic test device according to claim 6, wherein a height of at least one of the plurality of support bases from the lower housing is 0.6 mm or higher.

9. An immunochromatographic test device according to claim 1, wherein
   the upper housing includes a window frame having inclined portions for dropping a sample around the dropping hole, and the angle of the inclined surface in the developing direction is asymmetric between the upstream side and the downstream side of the development.

10. The immunochromatographic test device according to claim 9, wherein the upstream-side inclined portion in the developing direction is less inclined than the downstream-side inclined portion.

11. The immunochromatographic test device according to claim 10, wherein the dropping hole is in a rectangular shape, a width of the dropping hole in a width direction of the test strip is equal to the width of the test strip, and a length of the dropping hole in a longitudinal direction of the test strip is smaller than the width of the test strip.

12. The immunochromatographic test device according to claim 9, wherein the window frame is in a semicircular shape.

13. An immunochromatographic test device according to claim 1, wherein
- an inclined portion for observation is arranged around the detection window, the inclined portion in a width direction of the device is 30 degrees to 50 degrees, and the inclined portion in a longitudinal direction of the device is 40 degrees to 50 degrees.

14. An immunochromatographic test device according to claim 1, wherein
- a restricting wall lower than a height of the support bases is arranged on a top surface of the lower housing for guiding a leakage sample.

* * * * *